US009993343B2

(12) United States Patent
Smith

(10) Patent No.: US 9,993,343 B2
(45) Date of Patent: Jun. 12, 2018

(54) METHOD AND APPARATUS FOR PROTECTING MODULAR IMPLANT CONNECTION

(71) Applicant: Biomet Manufacturing, LLC, Warsaw, IN (US)

(72) Inventor: Aaron P. Smith, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 158 days.

(21) Appl. No.: 14/293,615

(22) Filed: Jun. 2, 2014

(65) Prior Publication Data

US 2014/0277556 A1 Sep. 18, 2014

Related U.S. Application Data

(62) Division of application No. 12/409,015, filed on Mar. 23, 2009, now Pat. No. 8,758,446.

(51) Int. Cl.
*A61F 2/36* (2006.01)
*A61B 17/16* (2006.01)
(Continued)

(52) U.S. Cl.
CPC ............ *A61F 2/36* (2013.01); *A61B 17/1668* (2013.01); *A61F 2/3607* (2013.01); *A61F 2/4607* (2013.01); *A61F 2/4637* (2013.01); *A61F 2/4684* (2013.01); *A61B 17/175* (2013.01); *A61F 2/0095* (2013.01); *A61F 2002/30332* (2013.01); *A61F 2002/30354* (2013.01); *A61F 2002/30474* (2013.01); *A61F 2002/30507* (2013.01); *A61F 2002/30604* (2013.01); *A61F 2002/30616* (2013.01); *A61F 2002/30718* (2013.01); *A61F 2002/30822* (2013.01); *A61F 2002/30828* (2013.01); *A61F 2002/3674* (2013.01); *A61F 2002/4622* (2013.01);
(Continued)

(58) Field of Classification Search
CPC ...... A61F 2/367; A61F 2/3676; A61F 2/3672; A61F 2002/365; A61F 2002/3625; A61F 2002/3652; A61F 2002/3627; A61F 2/36; A61F 2/3607; A61F 2/3609; A61F 2002/4642; A61F 2/4607
See application file for complete search history.

(56) References Cited

U.S. PATENT DOCUMENTS 3,818,514 A 6/1974 Clark
3,918,441 A 11/1975 Getscher
(Continued)

OTHER PUBLICATIONS

"Restoration® Modular Revision Hip System, Product Reference Guide for Cone/Conical and Broached/Fluted & Plasma Implants and Instruments," brochure, (2004) Stryker, pp. 1-12.
(Continued)

*Primary Examiner* — Christopher D Prone
(74) *Attorney, Agent, or Firm* — Schwegman Lundberg & Woessner, P.A.

(57) ABSTRACT

Apparatus and methods of protecting modular implant connection portions are provided. A guard includes an outer sidewall and an inner sidewall defining a cavity that covers a modular implant connection portion. The modular implant connection covered with the guard can facilitate test-fitting of other modular implant components and allows reaming of the tissue around the guard.

11 Claims, 7 Drawing Sheets

(51) Int. Cl.
*A61F 2/46* (2006.01)
*A61B 17/17* (2006.01)
*A61F 2/00* (2006.01)
*A61F 2/30* (2006.01)

(52) U.S. Cl.
CPC .............. *A61F 2002/4629* (2013.01); *A61F 2002/4641* (2013.01); *A61F 2220/0025* (2013.01); *A61F 2220/0033* (2013.01)

(56) References Cited

U.S. PATENT DOCUMENTS

| | | | |
|---|---|---|---|
| 4,227,265 A | 10/1980 | Frey | |
| 4,488,319 A | 12/1984 | von Recum | |
| 4,608,052 A * | 8/1986 | Van Kampen | A61F 2/30771 |
| | | | 428/687 |
| 4,676,797 A * | 6/1987 | Anapliotis | A61F 2/36 |
| | | | 623/23.45 |
| 4,963,155 A | 10/1990 | Lazzeri et al. | |
| 5,336,226 A * | 8/1994 | McDaniel | A61B 17/1666 |
| | | | 606/79 |
| 6,102,956 A * | 8/2000 | Kranz | A61F 2/3662 |
| | | | 623/23.15 |
| 6,238,436 B1 | 5/2001 | Lob et al. | |
| 6,264,699 B1 | 7/2001 | Noiles et al. | |
| 6,616,697 B2 * | 9/2003 | Sotereanos | A61B 17/175 |
| | | | 623/22.11 |
| 6,863,692 B2 | 3/2005 | Meulink | |
| 8,758,446 B2 | 6/2014 | Smith | |
| 2002/0099447 A1 * | 7/2002 | Mears | A61B 17/00234 |
| | | | 623/22.4 |
| 2002/0193882 A1 | 12/2002 | Koller | |
| 2004/0254646 A1 | 12/2004 | Stone et al. | |
| 2006/0015112 A1 | 1/2006 | McGovern | |
| 2007/0100464 A1 | 5/2007 | Meulink | |
| 2007/0244486 A1 | 10/2007 | Hogg et al. | |
| 2008/0021567 A1 * | 1/2008 | Meulink | A61B 19/026 |
| | | | 623/22.12 |
| 2009/0270867 A1 | 10/2009 | Poncet | |
| 2010/0241239 A1 | 9/2010 | Smith | |

OTHER PUBLICATIONS

"Restoration® Modular Revision Hip System Surgical Protocol, Restoration® Modular Cone Body/Conical Distal Stem Femoral Components Using the Restoration® Modular Instrument System," brochure, (2005) Stryker, pp. 1-21.

* cited by examiner

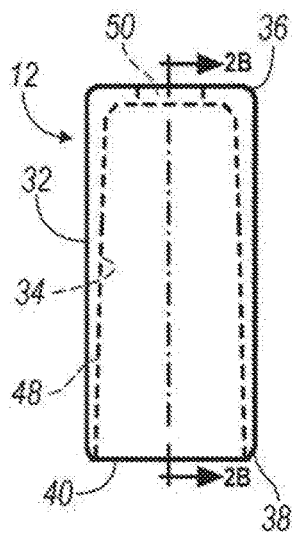
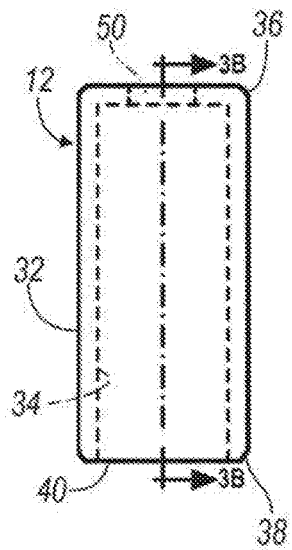
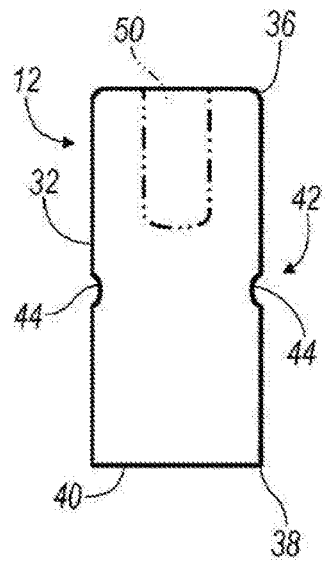
FIG. 2A  FIG. 3A  FIG. 4
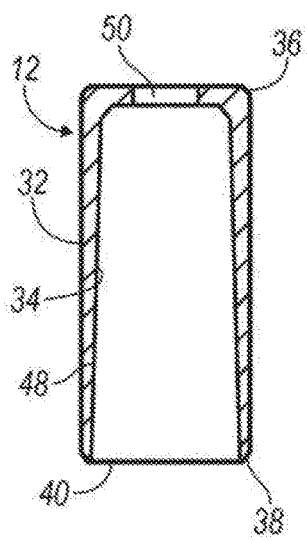
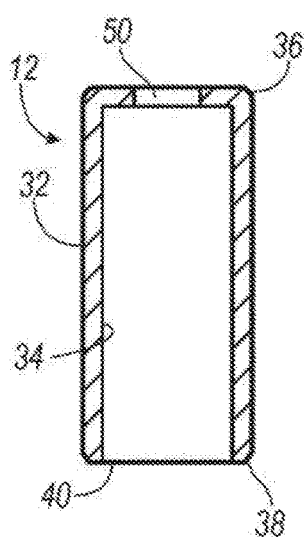
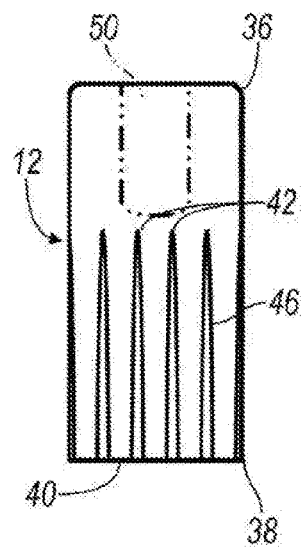
FIG. 2B  FIG. 3B  FIG. 5

METHOD AND APPARATUS FOR PROTECTING MODULAR IMPLANT CONNECTION

CROSS-REFERENCE TO RELATED APPLICATIONS

This application is a divisional of U.S. patent application Ser. No. 12/409,015 filed on Mar. 23, 2009, which issued as U.S. Pat. No. 8,758,466 on Jun. 24, 2014. The entire disclosure of the above application is incorporated herein by reference.

FIELD

The present disclosure relates to protecting a modular implant connection.

BACKGROUND

This section provides background information related to the present disclosure which is not necessarily prior art.

The need for articulating joint replacement may be due to injury, over use, trauma, or disease, for example. To repair the articulating joint, it may be necessary to implant the prosthesis into a long bone such that part of the prosthesis completely replaces the articulating end of the bone. Modular prostheses are often used in connection with long bones as they provide a customizable fit along the length of the prosthesis and are assembled intraoperatively. During the operative procedure, the surgeon may "trial" fit various components of the modular implant to accommodate the particular anatomy of the patient. Trial fitting of an implant may, however, leave regions of the implant exposed, including the connection points between the components of the modular implant.

SUMMARY

This section provides a general summary of the disclosure, and is not a comprehensive disclosure of its full scope or all of its features.

In various embodiments, the present teachings provide apparatus for and methods of protecting a modular implant connection portion including a guard having an outer sidewall and an inner sidewall and further defining a cavity.

Further areas of applicability will become apparent from the description provided herein. It should be understood that the description and specific examples are intended for purposes of illustration only and are not intended to limit the scope of the present disclosure. It should be further understood that while certain embodiments may illustrate an articulating joint, the apparatus and methods disclosed herein are useful for non-articulating modular implants as well.

DRAWINGS

The drawings described herein are for illustrative purposes only of selected embodiments and not all possible implementations, and are not intended to limit the scope of the present disclosure.

FIG. 2A is a side view of a guard according to various embodiments;

FIG. 2B is a cross-section of a guard along line 2B-2B of FIG. 2A according to various embodiments;

FIG. 3A is a side view of a guard according to various embodiments;

FIG. 3B is cross-section view of a guard along line 3B-3B of FIG. 3A according to various embodiments;

FIG. 4 is a side view of a guard having a grasping feature according to various embodiments;

FIG. 5 is side view of a guard having a grasping feature according to various embodiments.

Corresponding reference numerals indicate corresponding parts throughout the several views of the drawings.

DETAILED DESCRIPTION

Example embodiments will now be described more fully with reference to the accompanying drawings.

Figure 1:
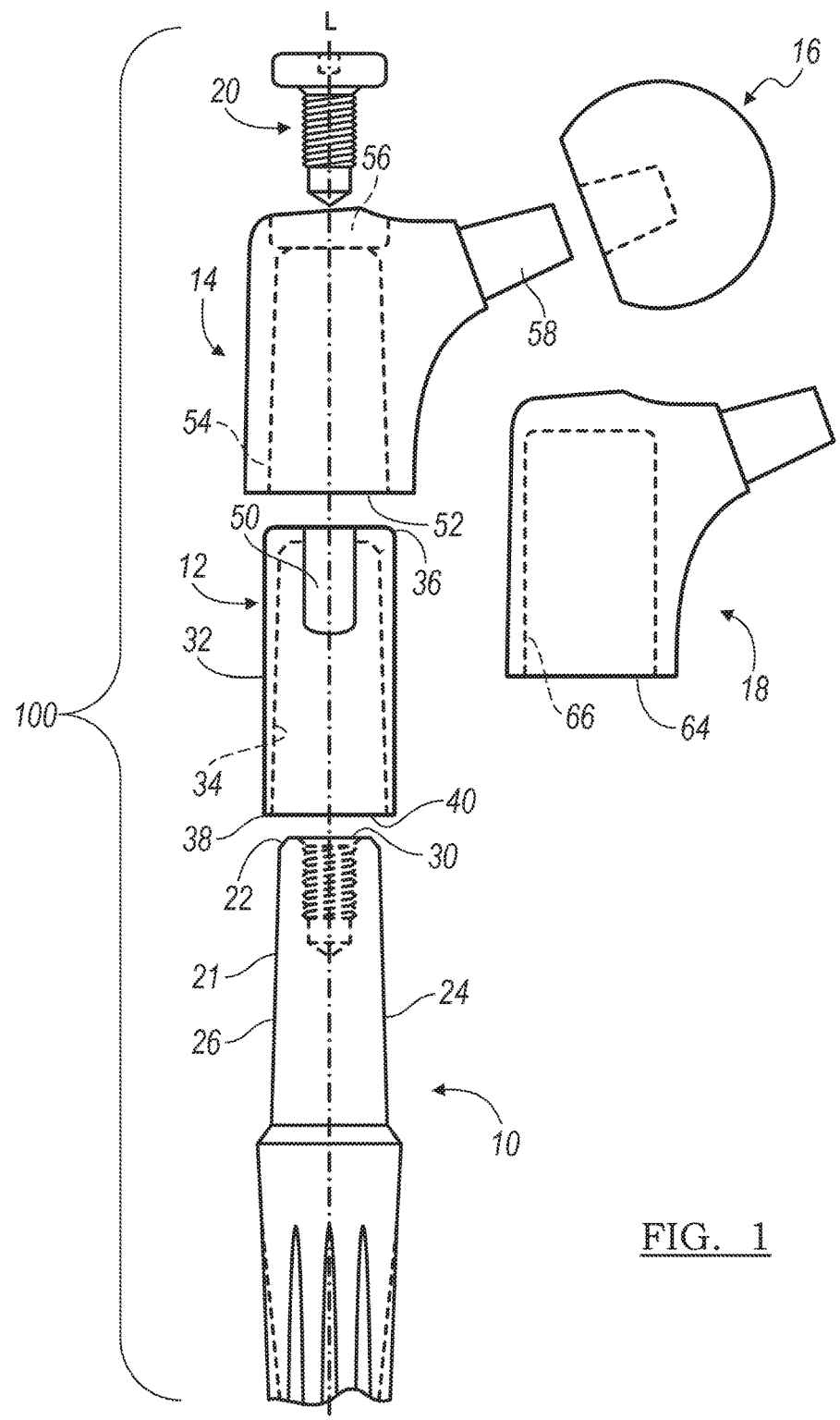
FIG. 1 is a side view of a modular femoral stem implant according to various embodiments.

Referring to FIG. 1, in various embodiments a modular implant system 100 is provided. The modular implant system 100 includes a distal stem 10 component, a guard 12, a proximal body 14, a femoral head 16, a trial 18, and a threaded bolt 20. The guard 12 protects at least one of the connection point 21 and proximal end 22 of the distal stem 10 component. The protection prevents any inadvertent scratching or damage to the distal stem 10 or the proximal body 14 while allowing test fitting using the trial 18 to simulate the size and fit of the proximal body 14 relative to the proximal end 22 of the distal stem 10. The modular implant system 100 can be provided as a kit which includes multiple combinations of each of the distal stem 10 component, guard 12, proximal body 14, femoral head 16, trial 18, and bolt 20. The combinations can include various sizes, lengths, and shapes of any of the modular implant system 100 components to facilitate ease of use and a customized fit.

The distal stem 10 is disposed into a long bone 200, as best illustrated in FIGS. 6A-6I. The distal stem 10 is shaped to accommodate insertion into the long bone 200 or repair site. Returning to FIG. 1, the proximal end 22 of the distal stem 10 includes a tapered outer surface 24 which mates with the guard 12. The proximal end 22 outer surface 24 is shaped as a Morse taper 26 to facilitate the locking fit or tapered fit connection with the proximal body 14 and corresponding tapered sidewall 54. The proximal end 22 of the distal stem 10 further defines a threaded distal stem bore 30 which extends partially through the distal stem 10 along a longitudinal axis L. As detailed later herein, the distal stem bore 30 facilitates securing of the modular implant system 100.

In various embodiments, the length of the Morse tapered region 26 of the distal stem 10 along the longitudinal axis is about 0.5 inches to about 3 inches. It is understood that the length of the Morse tapered region 26 can vary as the size of the distal stem 10 and the modular implant 100 vary to accommodate the particular needs of the patient.

The guard 12 can be made out of a biocompatible polymer, such as polyethylene or PEEK. In various embodiments, the guard 12 can be rigid or semi-rigid. The guard 12 is maintained on the proximal end 22 of the distal stem 10 through surface tension caused by the tight fit therebetween.

The guard 12 includes an outer cylindrical sidewall 32 and an inner sidewall 34. The inner sidewall 34 can be tapered as shown in FIGS. 2A and 2B, or the inner sidewall 34 can be cylindrical as shown in FIGS. 3A and 3B. Referring to FIGS. 2A and 2B, in embodiments where the inner sidewall 34 is tapered, the thickness of the guard 12 varies along the length of the guard 12 such that the thickness decreases from the proximal end 36 to the distal end 38.

Returning to FIGS. 2A-3B, the inner sidewall 34 mates with the outer tapered sidewall 24 of the proximal end 22 of the distal stem 10. The inner sidewall 34 of the guard 12 is disposed over the proximal end 22 of the distal stem 10 to provide a cap or cover over the proximal end 22 of the distal stem 10.

Turning to FIGS. 2A-5, the guard exterior 32 is substantially cylindrical. The cylindrical shape facilitates the test fitting of the trial 18 without causing the trial 18 to lock onto the guard 12 or, in other words, provides a readily removable and temporary engagement. The cylindrical exterior 32 of the guard 12 also facilitates use with other existing modular components.

In various embodiments, the guard 12 has an exterior diameter of about 0.25 inches to about 1 inch. Variations in the exterior diameter measurements of the guard 12 are within the scope of the present teachings to accommodate the particular needs of the patient and the various sizes of trials 18. Turning to FIGS. 4 and 5, the exterior 32 of the guard 12 can also include at least one grasping feature 42 by which the guard 12 can be grasped and manipulated. As shown in FIG. 4, an embodiment of the grasping feature 42 includes at least two recessed dimples 44. The dimples 44 can be used to grasp the guard 12 to remove it from the distal stem 10. As shown in FIG. 5, an embodiment of the grasping feature 42 includes a series of ridges 46 spaced about the exterior surface of the guard 12. While the ridges 46 of the depicted embodiment are vertical ridges, it is understood that the ridges 46 can also be horizontally disposed about a body of the exterior surface 32 of the guard 12.

As best shown in FIGS. 2A and 2B, the guard cavity 40 and the interior sidewall 34 have different cross-sections than the guard exterior 32. The guard cavity 40 and interior sidewall 34 define a Morse taper 48 cross-section along an inner diameter of the guard 12. The guard cavity 40 is mated to the Morse taper 26 at the proximal end 22 of the distal stem 10. The mated shape of the Morse tapers 26 and 48 provides a tight connection between the stem 10 and the guard 12, which protects the proximal end 22 of the distal stem 10 from debris. Although the fit differs, it is understood that the embodiment of FIGS. 3A and 3B also protect the proximal end 22 of the distal stem 10 from debris.

In various embodiments, the guard cavity 40 and the length of the guard 12 are substantially the same as those of the Morse tapered region 26 of the distal stem 10. Any difference in length may be an amount which is sufficient to provide adequate protection to the Morse tapered region 26 of the distal stem 10. As a non-limiting example, the variation between the length of the Morse taper region 26 and the guard cavity 40 can be less than about 15% or less than about 10%.

Referencing FIGS. 2A-5, the guard 12 further defines a bore 50 at the proximal or top end 36 of the guard 12, which in the depicted embodiment, is opposite to the guard cavity 40. As best shown in FIG. 1, when the guard 12 is disposed over the proximal end 22 of the distal stem 10, the bore 50 of the guard 12 and the bore 30 in the stem 10 are substantially aligned and concentric along longitudinal axis L.

Referring to FIG. 1, the proximal body 14 includes a cavity 52 which mates with the distal stem 10. The proximal body cavity area 52 is defined by a tapered sidewall 54 which provides a removable and adjustable fit with the Morse taper region 26 of the distal stem 10. The proximal body 14 further includes a bore 56 which concentrically aligns with the bore 30 of the distal stem 10. The proximal body 14 can mate with another component, such as the articulating head 16 of a hip implant via connection point 58.

Still referencing FIG. 1, the trial 18 includes a cavity 64 which mates with the distal stem 10. The cavity 64 is defined by a cylindrical sidewall 66 which provides a removable and adjustable fit with the guard 12 when the guard 12 is placed on the Morse taper region 26 of the distal stem 10. Generally, the trial 18 in the system 100 has substantially similar outer dimensions to those of the corresponding proximal body 14. One difference between the trial 18 and the proximal body 14 is that the trial 18 utilizes the cylindrical interior sidewall 66 to prevent locking with the cylindrical exterior 32 of the guard 12. As detailed in the surgical methods below, the trial 18 can be used to approximate which proximal body 14 will be used in the system 100 as implanted into the patient.

Turning to FIGS. 6A-6I, in various embodiments, methods of using the modular implant system 100 are provided. Generally, the distal stem 10 is inserted into a long bone 200 through a bone cavity 202 formed therein, such as the bone cavity 202 prepared in the intramedullary canal 204. The distal stem 10 is placed into the bone cavity 202 by impaction using a surgical hammer (not shown), as a non-limiting example. The area around the distal stem 10 is manipulated through reaming, contouring, or other techniques to provide clearance for the proximal body 14, as necessary. One or several trial bodies 18 are then placed on the guard 12 in a manner similar to that described previously in order to determine an appropriate size for the proximal body 14. For example, should a first trial body 18 not fit within the expanded bone cavity 202 or not provide a proper fit, the operator will continue to select other trial bodies 18 until an appropriate fit is achieved. After the appropriate proximal body 14 is selected, the guard 12 is removed from the distal stem 10. The cavity 52 of the proximal body 14 is then placed on top of the distal stem 10 at the proximal end 22 so that the proximal body 14 and the distal stem 10 are in locking engagement to secure the implant 100.

Figure 6A:
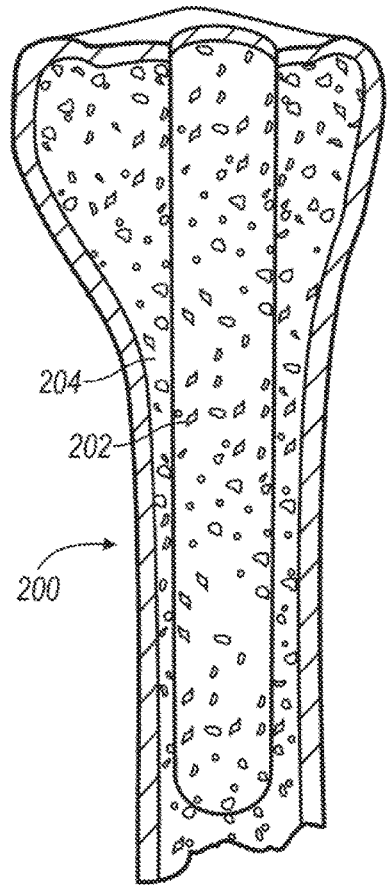
FIGS. 6A-6I depict a surgical method according to various embodiments.
Figure 6B:
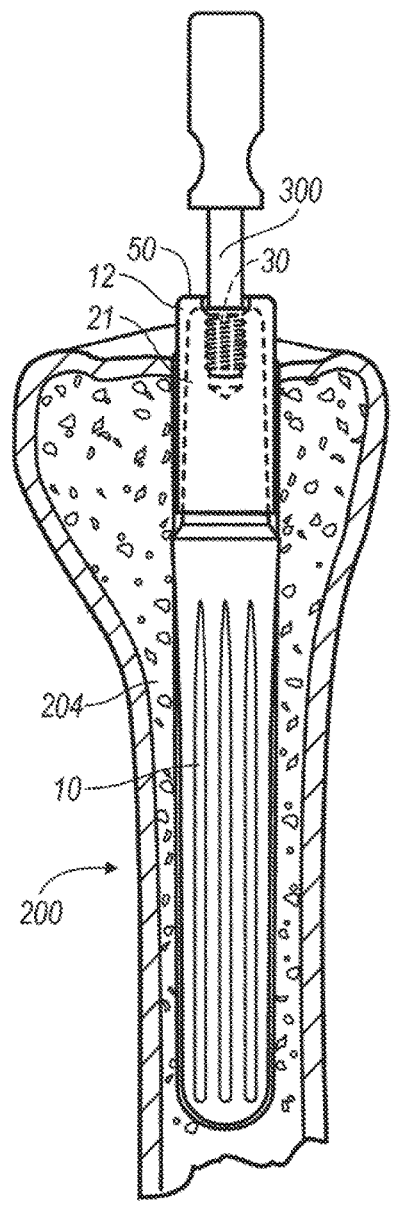

Referring to FIG. 6B, in various embodiments, to insert the distal stem 10 into the bone cavity 202 or intramedullary canal 204, a screw inserter 300 can be passed through the aligned opening defined by the distal stem 10 opening 30 and the bore 50 of the guard 12. It is noted that the screw inserter 300 can be aligned with the distal stem 10 via the guard bore 50 and the stem opening 30. Sufficient force is then applied to the screw inserter 300 to impact the distal stem 10 into the surrounding intramedullary canal 204 in any suitable manner. For example, a surgical hammer may be used to impact the screw inserter.

Figure 6C:
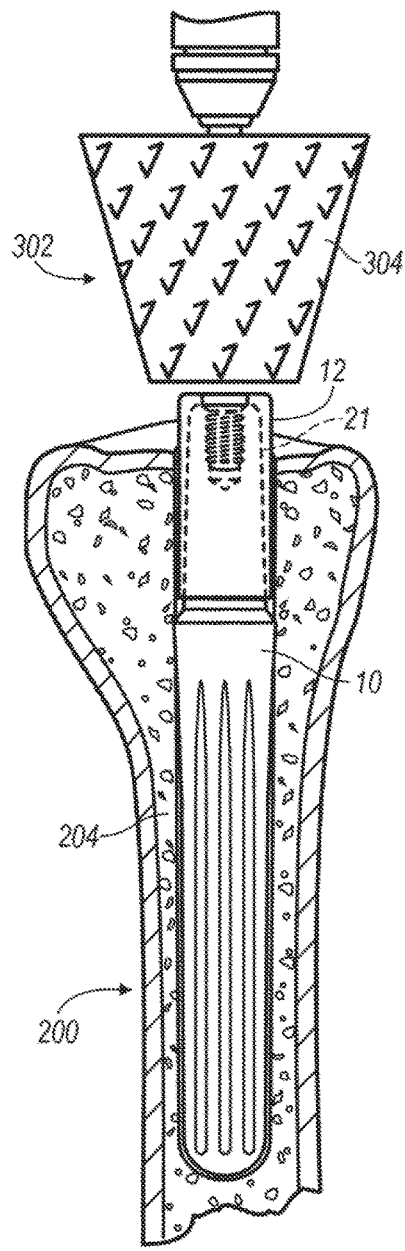
Figure 6D:
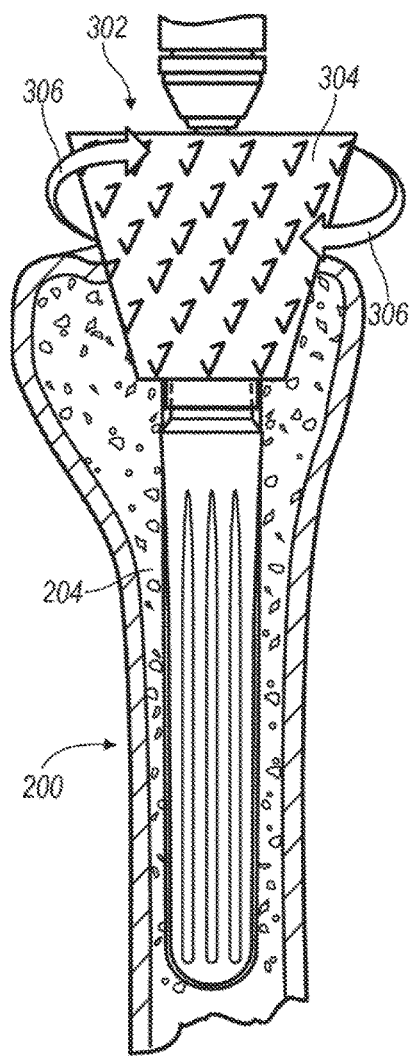

Referring now to FIGS. 6C and 6D, after the distal stem 10 is fixed into the bone cavity 202, the bone surrounding the proximal end 22 of the distal stem 10 can be reamed to accommodate the proximal body 14. The reaming is conducted around the guard 12, which remains in a fixed position during reaming, to protect the Morse taper 26 connection point of the distal stem 10. A reaming device 302 is disposed over the guard 12, and the reaming device 302 spins about the guard 12 as indicated by the arrows 306. Leaving the guard 12 in a fixed position during reaming protects the connection point 21. In addition, the guard 12 serves as a bearing surface for the reaming device 302.

In various embodiments, the reaming is performed in the bone 200 to a depth that is equal to the length of the guard 12. During the surgical procedure, a user can measure the height of the guard 12 and/or the size of the proximal body 14 and select a reamer 302 capable of forming an opening having an appropriate depth. This can be achieved by measuring the height of the guard 12 and selecting a reamer 302 having a bit 304 of substantially the same height as the guard 12. In such embodiments, maintaining the depth of reaming to substantially the same depth as the guard 12 protects the distal stem 10. In the embodiment illustrated in FIGS. 6C and 6D, the bit 304 has a conical shape to enlarge the bone cavity 202 in the surrounding bone 200. It is understood that a bit 304 having a non-conical shape, such as a cylinder as a non-limiting example, can also be used to enlarge the cavity 202. In various embodiments, the reaming device 302 can form a cylindrical bore, a partial cylindrical bore, or any other suitably shaped bore that mates with the cylindrical exterior surface 32 of the guard 12. The selected bit 304 will determine the shape of the opening about the guard 12. For example, the conical bit 304 will provide a conical shaped opening, while a cylindrical bit will provide a cylindrical shaped opening. In various embodiments, additional contouring, over that provided by the bit 304, of the bone 200 may be necessary to accommodate the proximal body 14. The additional contouring can be performed in any suitable manner, such as using a scalpel or a surgical drill, for example.

Figure 6E:
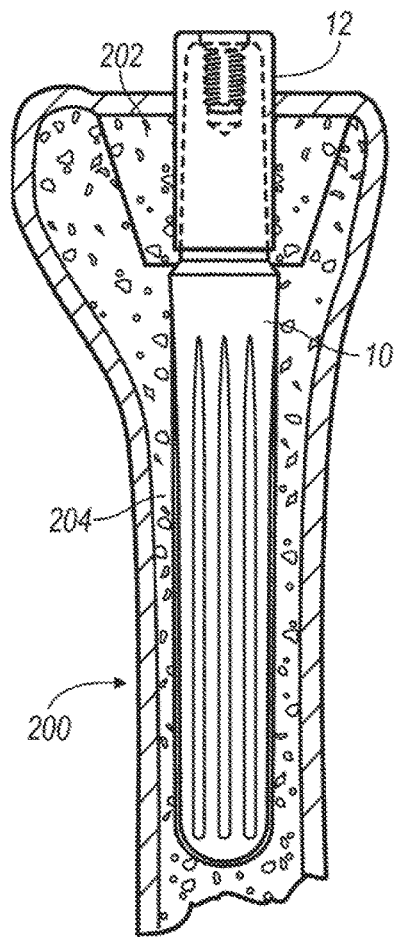
Figure 6F:
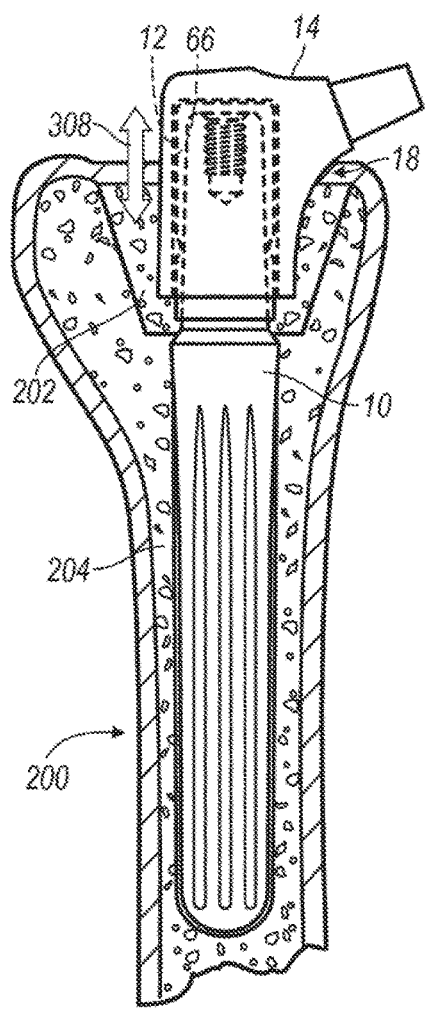

FIG. 6E shows a prepared bone cavity 202 in which the trial 18 can be tested for fit relative to the guard 12 on the distal stem 10. Turning to FIG. 6F, the cylindrical sidewall 66 of the trial cavity 64 is removably engaged with the cylindrical exterior 32 of the guard 12. The mating cylindrical shapes 32 and 66 prevent the two bodies from being locked together and provide an adjustable and removable temporary connection therebetween as indicated by arrow 308. Testing the trial 18 relative to the guard 12 on the distal stem 10 protects the Morse taper connection 26 of the distal stem 10. It is understood that a similar test-fitting can be conducted with the femoral head component 16 and connection point 58 of FIG. 1, as a non-limiting example.

Figure 6G:
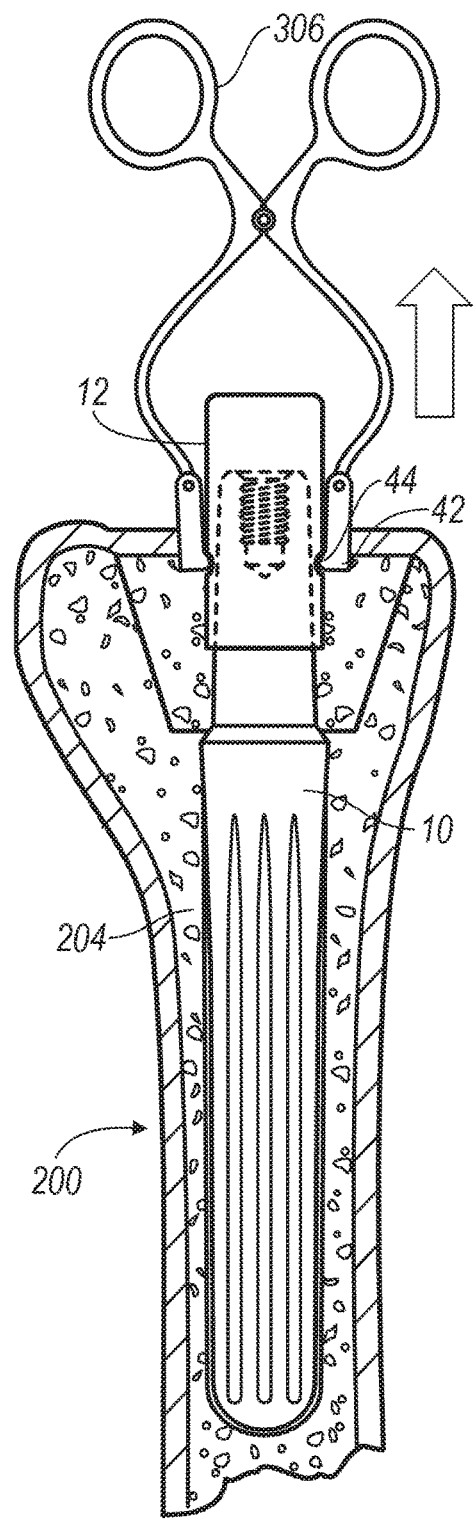
Figure 6H:
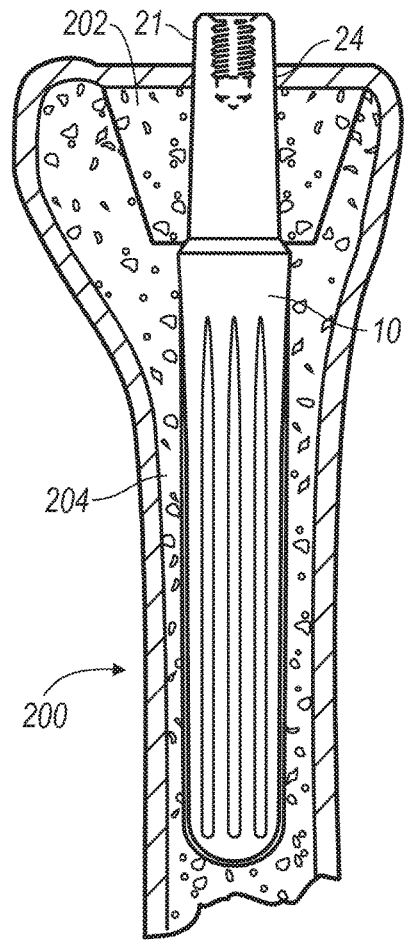

Turning to FIGS. 6G and 6H, after selecting the appropriate sized trial 18, the guard 12 can be removed from the distal stem 10 to expose the outer tapered sidewall 24 of the distal stem 10. The guard 12 can be grasped using the grasping feature 42 illustrated as recessed dimple 44 on the guard 12 with forceps 306, for example. It is understood that the guard 12 can also be removed using a pull-string or other implements.

Figure 6I:
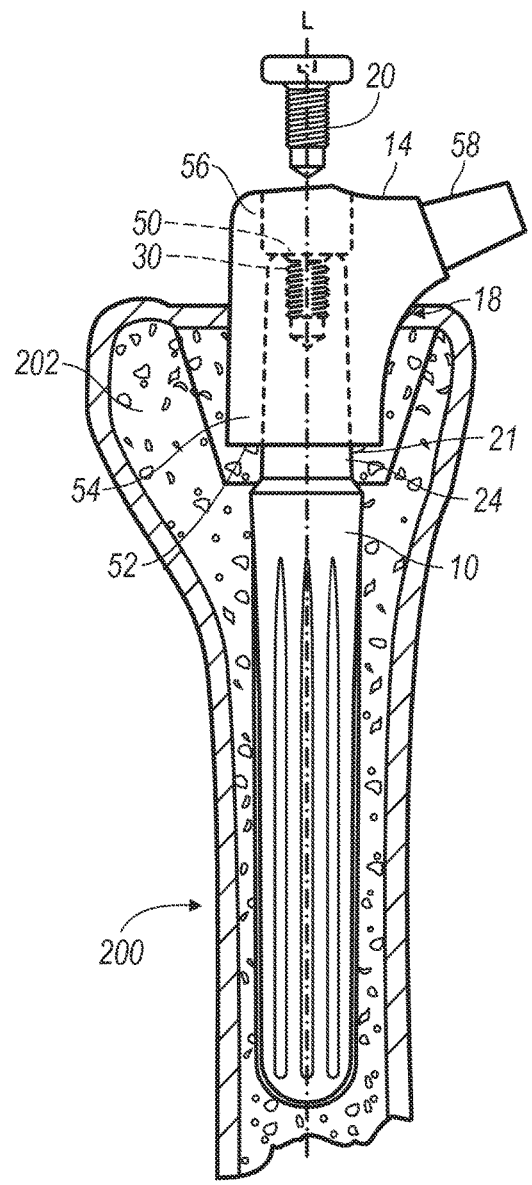

Turning to FIG. 6I, the proximal body 14, which corresponds to the selected trial 18, is then disposed over the exposed distal stem 10 and connection point 21 after the guard 12 is removed. The connection between the proximal body 14 and the exposed distal stem 10 provides a locked fit via the Morse taper interaction therebetween. In various embodiments, the system 100 can be secured using bone cement or other securing devices known in the art and in embodiments, the proximal body 14 and distal stem 10 can be secured using some combination of bolt 20, bone cement, or other securing devices.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A modular implant system, comprising:
   a guard having a cylindrical outer sidewall that has a grasping feature at an intermediate position on the cylindrical outer sidewall and an inner sidewall defining a cavity;
   a trial implant having a cylindrical interior sidewall that removably mates with the cylindrical outer sidewall of the guard;
   a first modular implant having a first modular implant connection portion, wherein at least a portion of the first modular implant connection portion of the first modular implant is received in the cavity to releasably mate the guard to the first modular implant connection portion during implantation of the first modular implant; and
   a second modular implant having an implant outer sidewall and a second inner sidewall defining a second cavity sized to receive the portion of the first modular implant connection portion of the first modular implant, wherein the implant outer sidewall is shaped and dimensioned differently from the cylindrical outer sidewall of the guard, wherein the second modular implant includes a second modular implant connection portion having a tapered interior sidewall that mates with a tapered exterior sidewall of the first modular implant connection portion;
   wherein the second modular implant is configured to separately and subsequently mate with the first modular implant at the first modular implant connection.

2. The system of claim 1, wherein the grasping feature includes recessed dimples formed into the cylindrical outer sidewall of the guard.

3. The system of claim 2, further comprising an instrument mateable to the grasping feature to facilitate removal of the guard from the modular implant connection portion.

4. The system of claim 1, wherein the guard is formed of a polymer.

5. The system of claim 4, wherein the guard is formed of polyethylene or PEEK.

6. The system of claim 1, wherein the guard further includes a top wall at a proximal end of the guard.

7. The system of claim 1, wherein the trial implant is substantially similar in shape to the second modular implant.

8. A modular implant system, comprising:
   a guard having:
   a proximal end and a distal end having a distal bore;
   a modular implant engaging inner sidewall extending between the proximal end and the distal end and that defines the distal bore;
   an outer sidewall forming a grasping feature at an intermediate position on the outer sidewall for positioning the guard on and removing the guard from an implant member of the modular implant system, wherein a portion of the outer sidewall is configured to engage a reamer when engaging the implant member of the modular implant to protect the modular implant while reaming a bone; and
   a trial proximal body to engage the portion of the outer sidewall of the guard when engaging the implant member of the modular implant to protect the modular implant while trialing with the trial proximal body.

9. The system of claim 8, wherein the grasping feature includes at least one of:

two recessed dimples, wherein the two recessed dimples are configured to be engaged to grasp the guard; or two ridges, wherein the two ridges are configured to be engaged to grasp the guard.

10. A modular implant system, comprising:

a distal stem having a proximal end configured to receive a threaded bolt;

a proximal body having an internal body bore and a connection point;

a femoral head engagable to the connection point of the proximal body; and a guard having an exterior surface that is substantially cylindrical and including:
  at least one grasping feature,
  an interior surface shaped to mate with the distal stem,
  a proximal bore, and
  a distal bore;

wherein the distal bore of the guard receives the proximal end of the distal stem such that the guard is positioned over the proximal end of the distal stem and the proximal body receives the exterior surface of the guard within the internal body bore such that the proximal body is positioned over the guard and the proximal end of the distal stem.

11. The system of claim 10, wherein the grasping feature is one of recessed dimples or ridges.

* * * * *